United States Patent [19]
Elias

[11] Patent Number: 5,456,013
[45] Date of Patent: Oct. 10, 1995

[54] INDUCTIVE TILT SENSOR AND METHOD FOR MEASURING TOOTH MOBILITY

[76] Inventor: Sharon A. Elias, 420 E. 72nd St., No. 8K, New York, N.Y. 10021

[21] Appl. No.: 245,156

[22] Filed: May 17, 1994

Related U.S. Application Data

[63] Continuation-in-part of Ser. No. 95,579, Jul. 19, 1993, abandoned.

[51] Int. Cl.⁶ ..................................................... G01C 9/06
[52] U.S. Cl. ................................. 33/366; 33/513; 433/27
[58] Field of Search ............................. 33/356, 365, 366, 33/377, 513; 336/135, 136; 324/207.15, 207.23, 207.24, 207.25; 433/27, 72; 128/776, 777

[56] References Cited

U.S. PATENT DOCUMENTS

| 2,427,866 | 9/1947 | MacGeorge | 336/136 |
| 3,184,861 | 5/1965 | Conrad | 33/366 |
| 3,235,790 | 2/1966 | Collins . | |
| 3,358,377 | 12/1967 | Martin et al. | 33/366 |
| 3,839,904 | 10/1974 | Stripling et al. | 33/366 |
| 3,911,592 | 10/1975 | Crask | 33/366 |
| 3,921,114 | 11/1975 | Bridewell et al. | 336/135 |
| 3,943,913 | 3/1976 | Johnson | 433/27 |
| 3,984,918 | 10/1976 | Chaney | 33/366 |
| 4,034,476 | 7/1977 | Johnson | 433/27 |
| 4,098,364 | 7/1978 | Schedrovitsky et al. | 336/135 |
| 4,157,619 | 6/1979 | Zuvela | 33/366 |
| 4,507,965 | 4/1985 | Stratton et al. | 33/366 |
| 4,676,103 | 6/1987 | Nakajima | 33/366 |
| 4,821,423 | 4/1989 | Adams | 33/366 |
| 4,945,274 | 7/1990 | Pernpeintner | 336/135 |
| 4,991,301 | 2/1991 | Hore | 33/336 |
| 5,293,979 | 3/1994 | Levasseur . | |
| 5,317,299 | 5/1994 | Dhyanchand et al. . | |

FOREIGN PATENT DOCUMENTS

| 2594536 | 9/1987 | France | 33/366 |
| 3-245013 | 10/1991 | Japan | 33/366 |
| 2211942 | 7/1989 | United Kingdom | 33/366 |

Primary Examiner—William A. Cuchlinski, Jr.
Assistant Examiner—G. Bradley Bennett
Attorney, Agent, or Firm—Amster, Rothstein & Ebenstein

[57] ABSTRACT

A sensor for measuring angular displacement of a small body comprising a sealed housing containing a differential transformer having at least two primary coils, one primary and two secondary coils, or two primary and two secondary coils, said coils being partially submerged in a ferromagnetic fluid. Upon application of an AC current to at least the primary coils of the differential transformer, the voltage across the circuit defined by the two primary or the two secondary coils is indicative of the angle of tilt of the sensor and the body to which it is attached.

33 Claims, 6 Drawing Sheets

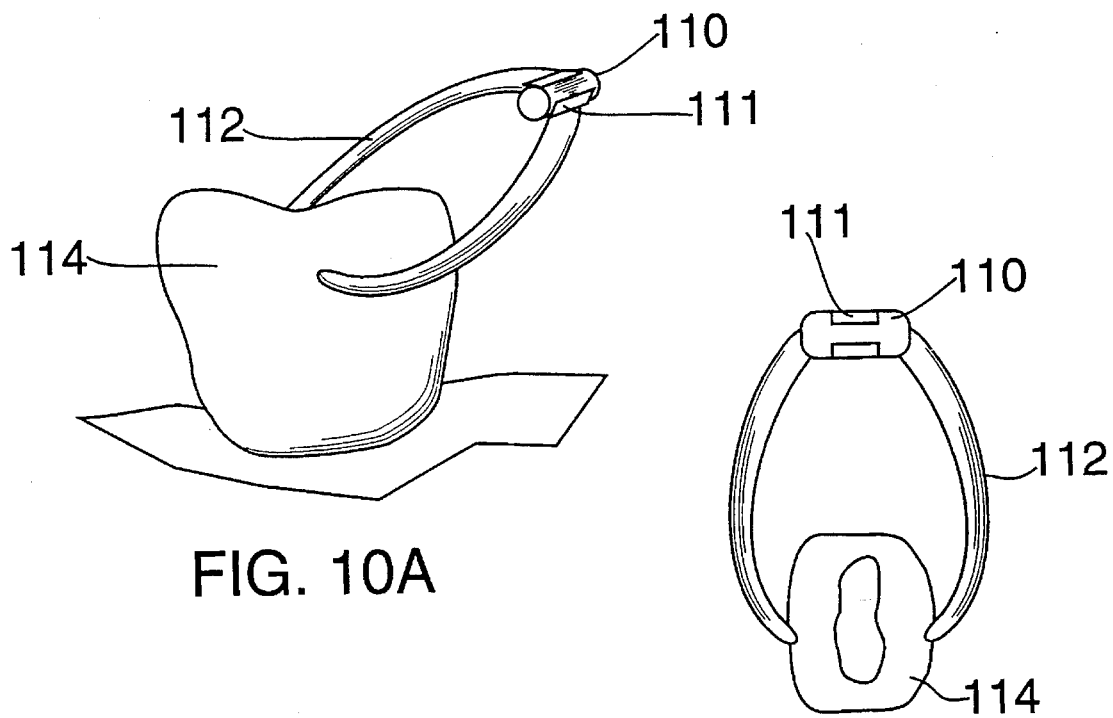
FIG. 10A
FIG. 10B
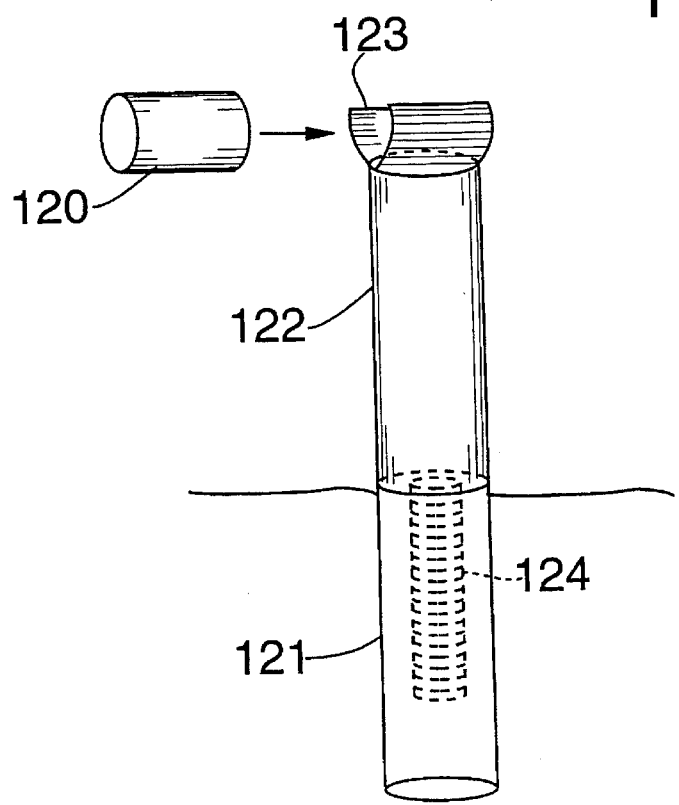
FIG. 11

INDUCTIVE TILT SENSOR AND METHOD FOR MEASURING TOOTH MOBILITY

This a continuation-in-part application of Ser. No. 08/095,579, filed Jul. 19, 1993 now abandoned.

FIELD OF THE INVENTION

The invention relates generally to the field of sensing the tilt or angular displacement of a body. More specifically, it relates to the precise measurement of the small-scale, relatively minimal tilt or angular displacement of a body, such as a tooth or dental implant anchor.

BACKGROUND OF THE INVENTION

In the field of dentistry, it is necessary to measure the mobility or angular displacement of a tooth or dental implant to predict the long term integrity of the tooth or implant. In particular, in preparation for securing a crown to an implanted fixture, the integrity of the implant in the patient's jaw must be tested. Generally, an opening is created in the patient's jaw and a setting for the fixture is inserted into the opening. The setting materials have been developed to be highly compatible with human bone, whereby under ideal circumstances, the patient's bone tissue surrounding the setting osseointegrates and effectively incorporates the setting into the jaw structure. After a reasonable healing period, the integrity of the setting in the jaw is evaluated. If there is any movement of the setting, it is concluded that the setting has not adapted sufficiently to the jaw to support a dental implant. Similarly, for an existing tooth, it may be concluded that the tooth is not sufficiently rooted in the mouth structure to sustain normal use without additional support in the form of bridges, etc.

Available tooth displacement sensors are detailed in the article entitled "Review of Methods for Measuring Tooth Mobility" by Dr. Samuel Yankell, which was published in 1988 in the *Compendium of Continuing Education*, Dental Supplement No. 12, pages S428–S432. As detailed therein, early sensors comprised calipers which recorded the physical displacement of the tooth in response to pressure applied thereto. Assessing the exact amount of pressure to which the tooth is subjected is difficult in such a system. Furthermore, the caliper-based systems were inexact given the fact that the calipers themselves often move in response to the applied pressure, thereby influencing the measurements. Later sensors have been developed to measure tooth mobility without the application of an external force to the tooth and measuring tool. Eddy current displacement sensors, holographic interferometers, and stereophotography systems have been used to measure tooth mobility without the measuring tool physically contacting the tooth and thereby, to some degree, physically influencing the tooth movement. Each of the foregoing systems is able to take a "picture" of the tooth under various load conditions, which conditions simulate either expected dental procedures or normal usage to which the tooth or fixture will be subjected. An analysis of the "pictures" provides a profile of the tooth or fixture mobility. A disadvantage of the latter methods of measurement is the need to rely on an external standard by which the movement observed in successive "pictures" is correlated to actual displacement in response to a load.

In unrelated technologies, tilt sensors have been developed utilizing several basic approaches. Low gravity accelerometers utilizing force balance spring mechanisms provide highly accurate tilt angle measurement; however, such systems are large in size incorporating high cost, complex electromechanical transducers. Though appropriate for large scale tilt or attitude measurements, such as for aeronautic applications, such sensors cannot be scaled to be workable in smaller dimensions.

Another category of angular measurement devices rely on the use of a variable capacitor or variable resistor positioned in an enclosure which is partially filled with either a dielectric or a conductive fluid. Upon angular displacement of the enclosure, the movement of the air bubble above the fluid is detected by measurement of the change in the electrical capacitance or resistance.

An angular displacement sensor is provided in U.S. Pat. No. 3,839,904 of Stripling, et al, which is entitled "Magnetic Fluid Level Detector And Vibration Transducer". The Stripling, et al sensor provides a magnetic fluid sensing element having a primary coil and two secondary coils disposed about a vial which is partially filled with fluid. A single magnetic flux path passes through the primary and the two secondary coils, with a portion of the flux path being in the air gap about the fluid in the vial. Angular displacement of the vial results in displacement of the fluid and a consequent change in the magnetic field, resulting in an output voltage indicative of the displacement. Such a sensor must be relatively large in size in order to compensate for the large presence of an air gap in conjunction with sufficient ferromagnetic fluid for the desired magnetic permeability.

U.S. Pat. No. 4,676,103 of Nakajima provides "Acceleration or Inclination Sensors" which operate in a similar manner to the above-noted category of systems. The Nakajima sensors effectively utilize a bubble of magnetic fluid which is displaced in response to angular displacement of its housing.

Some disadvantages of the sensors which rely in part on the air bubble or air gap in the sensor enclosure include variability in readings due to ambient temperature fluctuations, relatively low output signal levels due to the fact that air is a high reluctance path for magnetic flow, and lack of scalability to ideal dimensions given the need to increase fluid amounts to compensate for the high reluctance air path.

What is desired, therefore, is a system which provides high output signals, representative of angular displacement, in a small-scale, temperature stable sensor.

It is, therefore, an objective of the present invention to provide a system and method for measuring angular displacement of a body on a small scale.

It is another objective of the invention to provide a system and method for measuring angular displacement of a body without requiring external calibration.

It is still another objective of the invention to provide a system and method by which angular displacement of a body can be measured without applying force to the measurement tool itself and thereby affecting the results of the measurement.

Yet another objective of the invention is to provide an angular displacement sensor which can effectively provide high output signals representative of angular displacement in a small-scale, temperature-stable sensor.

SUMMARY OF THE INVENTION

These and other objectives of the invention are realized by the inventive angular displacement sensor which comprises an AC power source, a variable differential transformer having two primary coils, or at least one primary coil and two secondary coils, means for measuring voltage output from the transformer, and a reservoir of ferromagnetic fluid, which fluid selectively contacts the two coils and, when displaced in proportion to the angular displacement of the body to which the sensor is attached, changes the magnetic flux path and thereby the relative inductance in the coils to produce an output voltage. The output voltage will be proportional to the tilt angle and its phase will be indicative of the direction of tilt. The transformer can be mounted on a clamp which is adapted to engage the body, such as the tooth or fixture, for which displacement is to be measured.

BRIEF DESCRIPTION OF THE INVENTION

The invention will now be described with reference to the attached drawings wherein:

FIG. 1 provides a schematic illustration of a first embodiment of the invention having only first and second primary coils.

FIG. 2 provides a schematic illustration of a second embodiment of the invention including first and second primary and first and second secondary coils.

Figure 5:
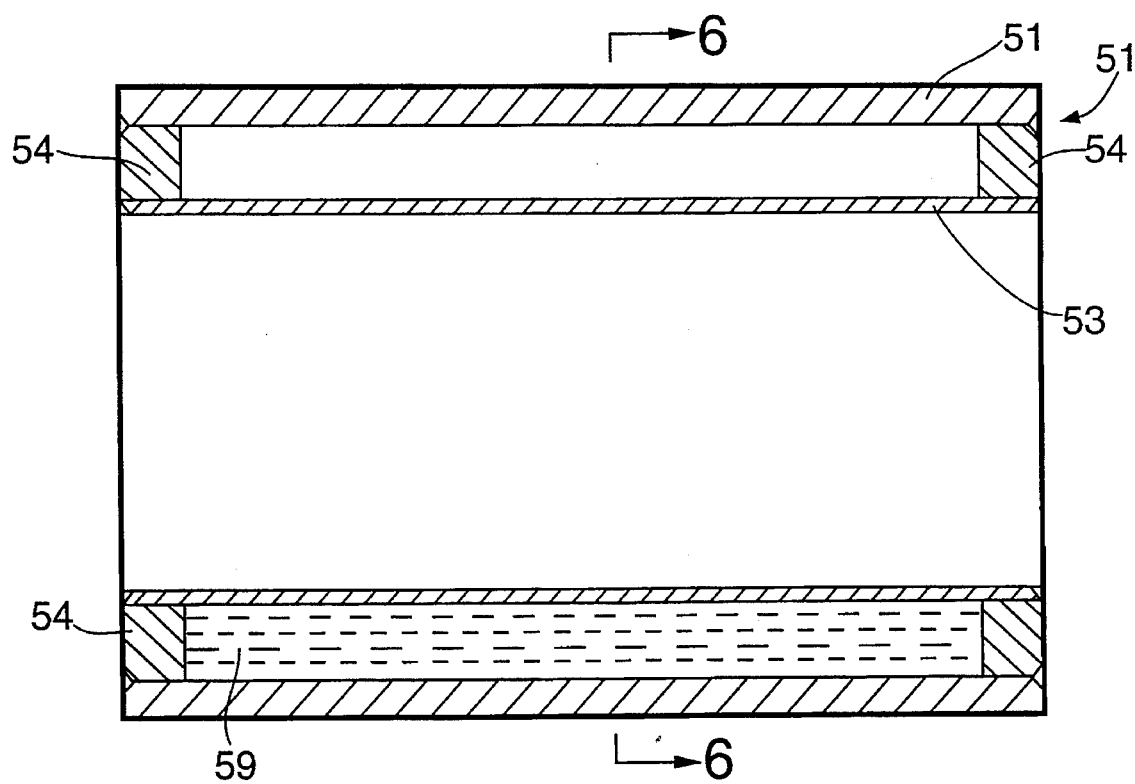

FIG. 5 provides a schematic illustration of the cylindrical member having an annular channel as utilized in several embodiments of the invention.

Figure 6:
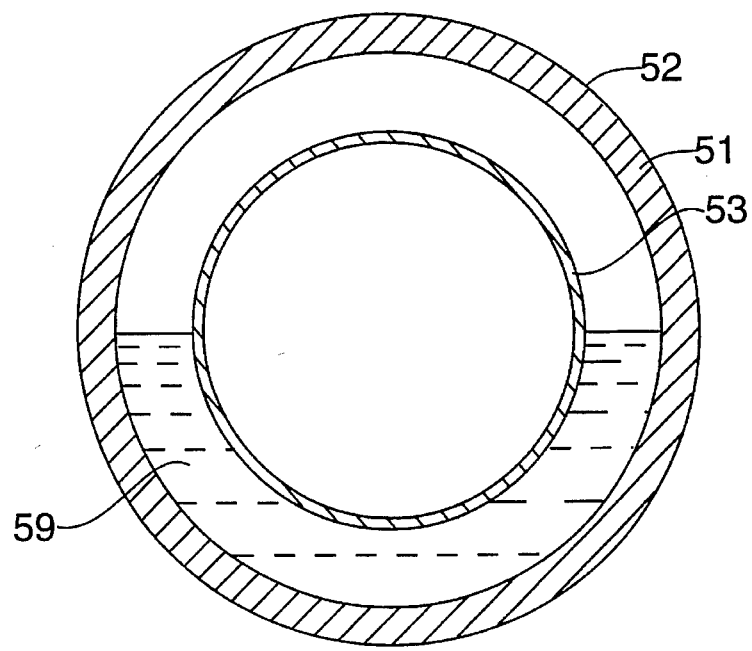

FIG. 6 is a cross-section of the cylindrical member having an annular channel as utilized in several embodiments of the invention.

Figure 7:
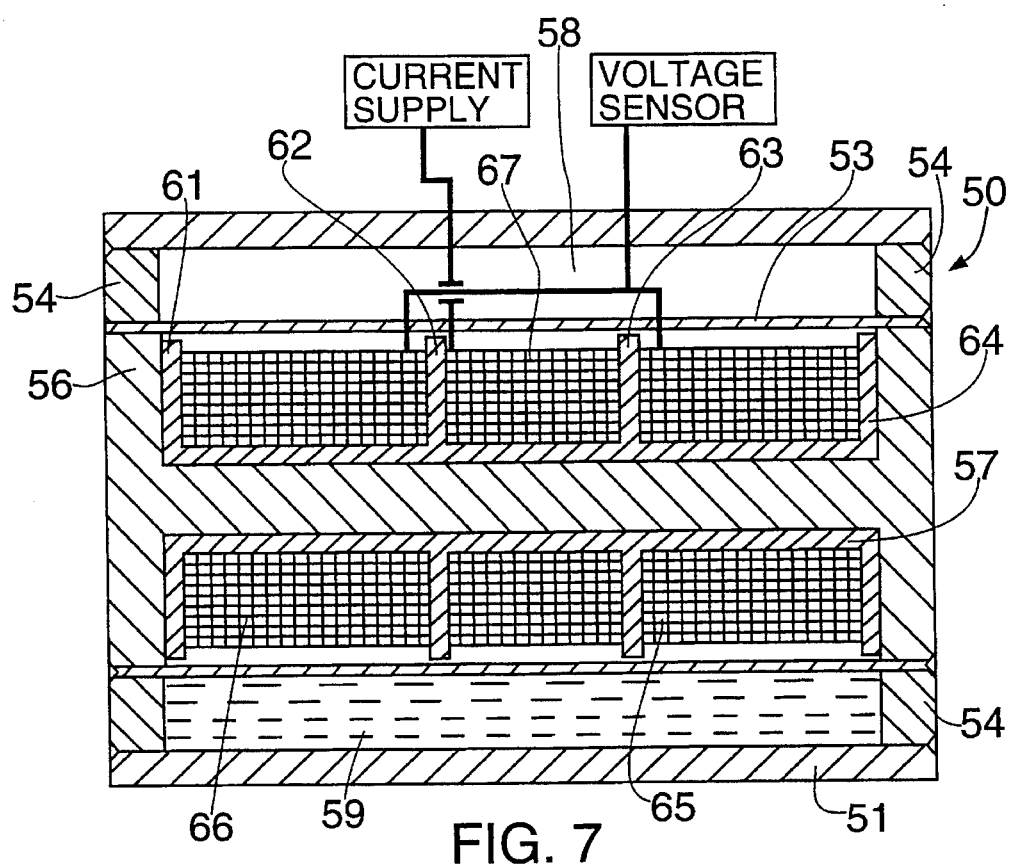

FIG. 7 provides a schematic illustration of the third embodiment of the invention having a single primary and two secondary coils positioned about a frame in the opening defined by the longitudinal axis of a cylindrical member having an annular channel.

Figure 8:
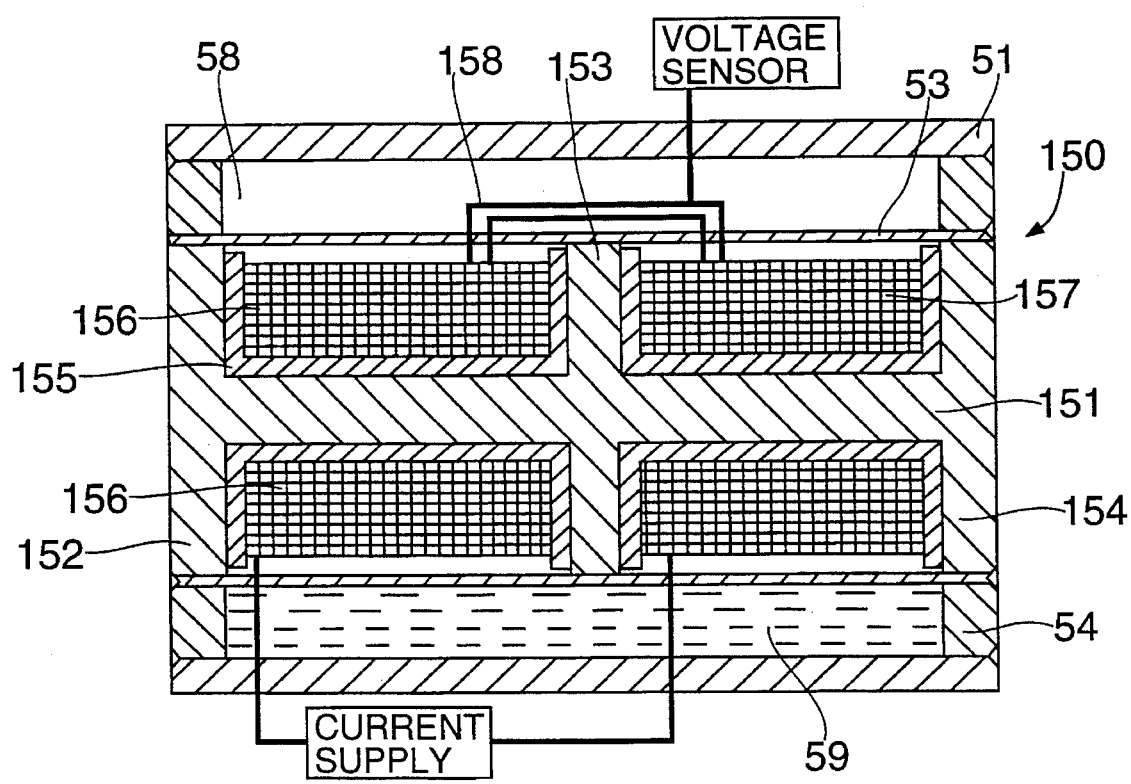

FIG. 8 provides a schematic illustration of a fourth embodiment of the invention having two primary coils positioned about a frame in the opening defined by the longitudinal axis of a cylindrical member having an annular channel.

Figure 9:
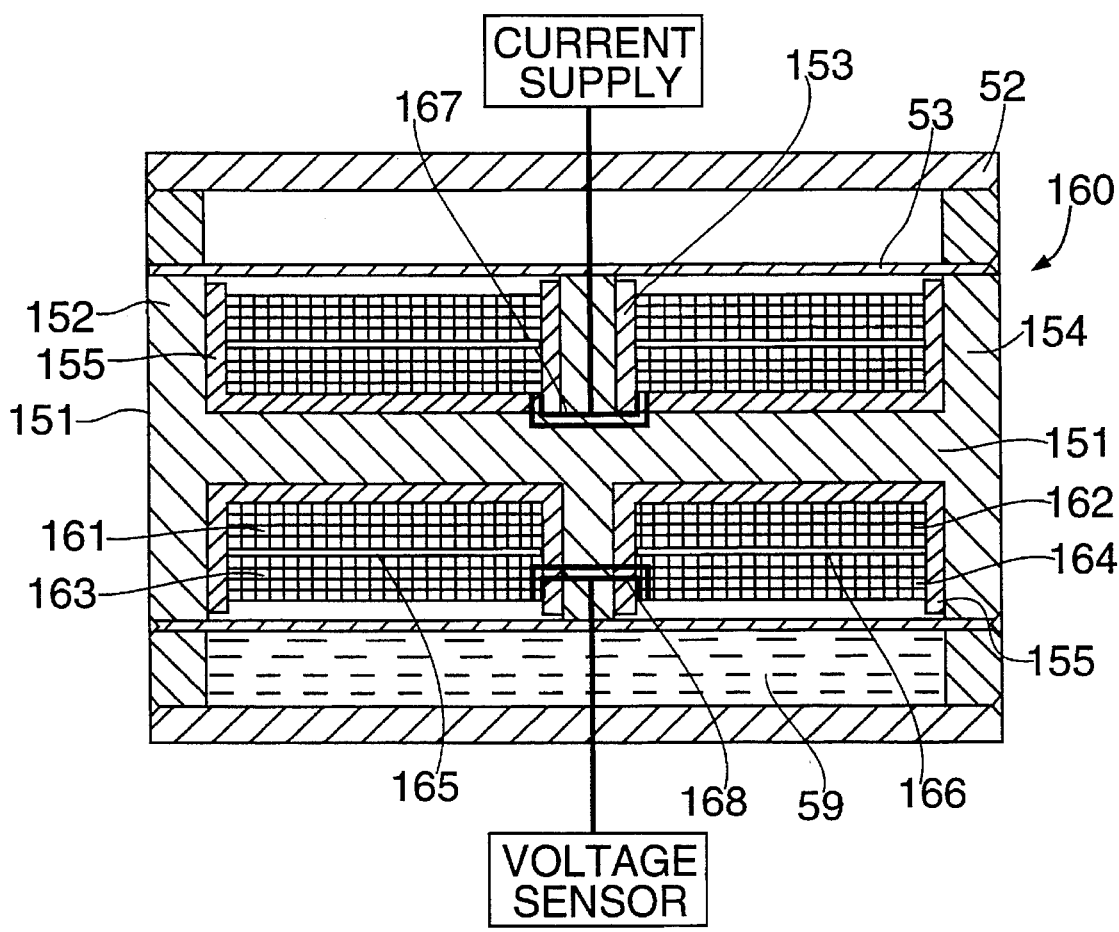

FIG. 9 provides a schematic illustration of a fifth embodiment of the invention having two primary and two secondary coils positioned about a frame in the opening defined by the longitudinal axis of a cylindrical member having an annular channel.

FIGS. 10A and 10B illustrate the inventive sensor mounted in a clamp adapted for attaching to a body, i.e., a tooth, for conducting the inventive angular measurements.

FIG. 11 illustrates the inventive sensor mounted in a member adapted for attaching to a body, i.e., a provisional component, an impression coping, or an abutment on an implanted dental fixture, for which angular displacement is to be measured.

DETAILED DESCRIPTION OF THE PREFERRED EMBODIMENT

Figure 1:
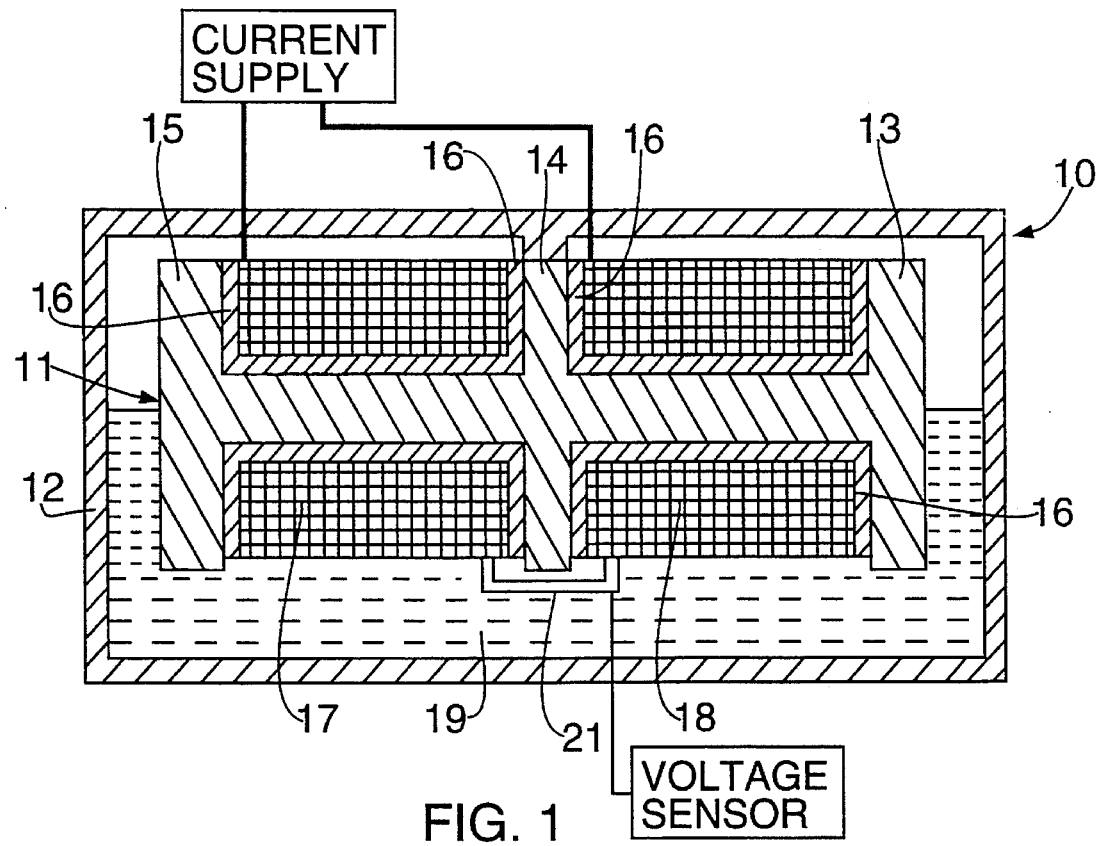

A first embodiment of the invention, as illustrated in FIG. 1, is a single axis tilt sensor, 10. The housing, 12, of sensor 10 is a sealed housing which is fabricated of plastic or non-ferromagnetic metal and has a lower edge which is flat with respect to the plane of gravity. An elongated coil form, 11, is disposed in housing 12. The coil form 11 is made of ferromagnetic material, such as iron, ferrite, etc., and is configured to include flanges 13, 14 and 15 extending in the radial direction from the central axis of the form, with at least the center flange 14 being attached to housing 12. A first primary coil 17 of insulated electrically conductive wire is wound about coil form 11 in the opening defined by flanges 15 and 14. A second primary coil 18 of insulated electrically conductive wire is wound about coil form 11 in the opening defined by flanges 14 and 13. Coils 17 and 18 may comprise enamel-coated copper wire and are connected to each other, at junction 21. The primary coils 17 and 18 are preferably connected in series opposition, as will be detailed below in the discussion of the operation of the sensor; although, an alternative embodiment in which the coils are connected in series aiding is also noted. An AC power source (not shown) is connected to supply a current to the sensor coils and a meter (also not shown) is connected to measure the output of the sensor coils as a function of the angular displacement of the sensor.

The openings in the coil form, the first being defined by flanges 15 and 14 and the second being defined by flanges 14 and 13, may each additionally be provided with a bobbin 16 of insulated material such as plastic. The bobbins 16 provide additional insulation between the coil form and the coils and can physically facilitate the placement of the windings of the coils 17 and 18. Housing 12 is sealed and is partially filled with a ferromagnetic fluid 19, to a level at which the coil form 11 is partially submerged in the fluid.

In operation, a source of alternating current is applied to the terminals of coil 17 and coil 18, which are connected at junction 21 in series opposition. The current through coil 17 will generate a magnetic flux in a path about the submerged portion of coil 17 in the opening defined by flanges 15 and 14. The current through coil 18 will generate magnetic flux in a path about the submerged portion of coil 18 in the opening defined by flanges 14 and 13, which path is reverse in direction to the flux generated by coil 17. Therefore, the two magnetic fluxes will flow in the same direction through flange 14 and into ferromagnetic fluid 19, wherein the magnetic fluxes will separate into two flux flows, flowing in opposite directions around the submerged portions of coils 17 and 18, and back into coil form 11 at flanges 15 and 13, respectively. It is also to be noted that the relationship of the dimensions of the coil form to the dimensions of the housing and the amount of ferromagnetic fluid contained in the "partially-filled" housing are chosen to optimize low reluctance magnetic flux paths about the coils, such that the paths not pass through air. In the horizontal position, the flux flowing through coil 17 will be of the same magnitude as the flux flowing through coil 18, and therefore, the impedance of coil 17 will be equal to the impedance of coil 18. The foregoing conclusion as to flux and impedance relies on the ideal condition in which the number of windings, or turns of wire in each coil, is the same. It is not necessary that the number of windings be the same since the system can readily be calibrated to account for differences in the number of windings, as it can for wire material differences or any other factors which would impact the magnetic flux and impedance relationship between the first and second primary coils. For the equal windings, horizontal sensor example, the voltage measured at the junction 21 of coil 17 and coil 18 will be one-half of the voltage of the input current source.

When the tilt sensor 10 is angularly displaced along its longitudinal axis, wherein the bottom surface of the sensor is no longer in a horizontal position, the ferromagnetic fluid 19 will stay horizontal due to gravity. Therefore, the impedance of coil 17 will not be equal to the impedance of coil 18.

Figure 3:
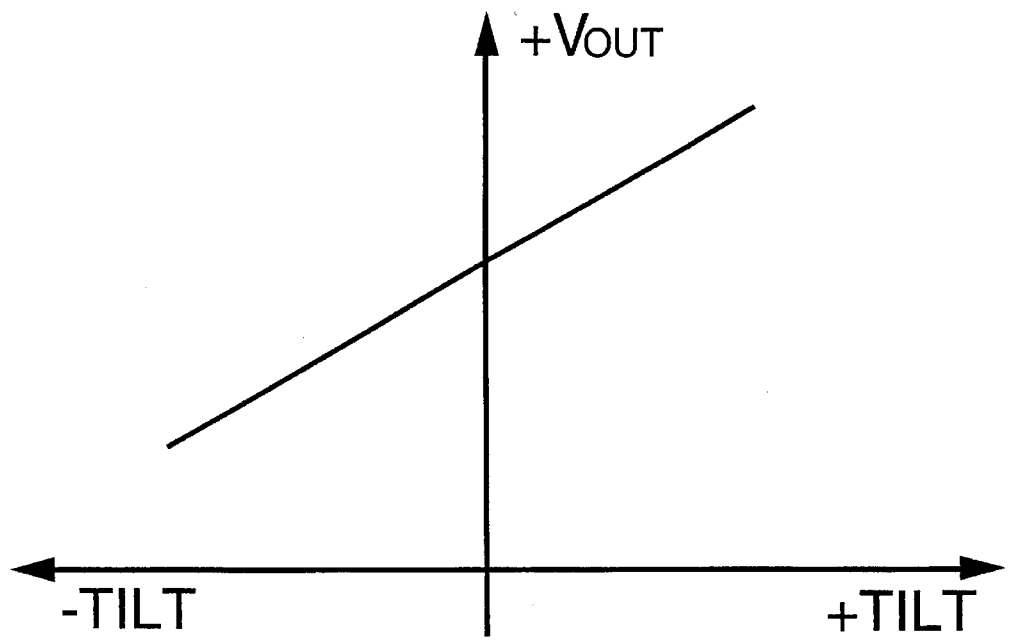
FIG. 3 is a graph illustrating the voltage output: tilt angle relation for the first embodiment of the invention.

The voltage measured at the junction 21 of coil 17 and coil 18 will be either lower or higher than the voltage measured at junction 21 when the sensor was in a horizontal position, depending upon the direction of tilt. FIG. 3 provides a graph illustrating the voltage measured at the junction 21 of the coils 17 and 18 as a function of different angles of tilt. Any measured voltage can then be correlated to the respective angle of tilt.

An alternative embodiment of the FIG. 1 sensor 10 has coils 17 and 18 connected in series aiding with the alternating current source connected to the circuit defined by coils 17 and 18. The magnetic flux path generated by coil 17 will flow in the same direction as the magnetic flux path generated by coil 18. In this instance, when the sensor 10 is placed in a horizontal position, there will be no detectable flux through flange 14, since the flux of coil 17 and the flux of coil 18 are equal in magnitude and are flowing in opposite directions through the flange 14 so as to cancel each other. The impedance of coil 17 will be equal to the impedance of coil 18, due to the flux magnitude in coil 17 being equal to the flux magnitude in coil 18. Therefore, the voltage measured at the junction of coils 17 and 18 will be one-half of the voltage of the current source applied to the series circuit defined by coils 17 and 18.

When the series aiding tilt sensor 10 is tilted along its longitudinal axis, the amount of ferromagnetic fluid surrounding coil 17 will be different from the amount of ferromagnetic fluid surrounding coil 18. Therefore, some magnetic flux will flow through flange 14, and the impedance of coil 17 will no longer be equal to the impedance of coil 18. The change in the voltage measured at the junction of coils 17 and 18 will be a function of the tilt, with the increase or decrease of the voltage again being a function of the direction of the angular displacement of the sensor.

Figure 2:
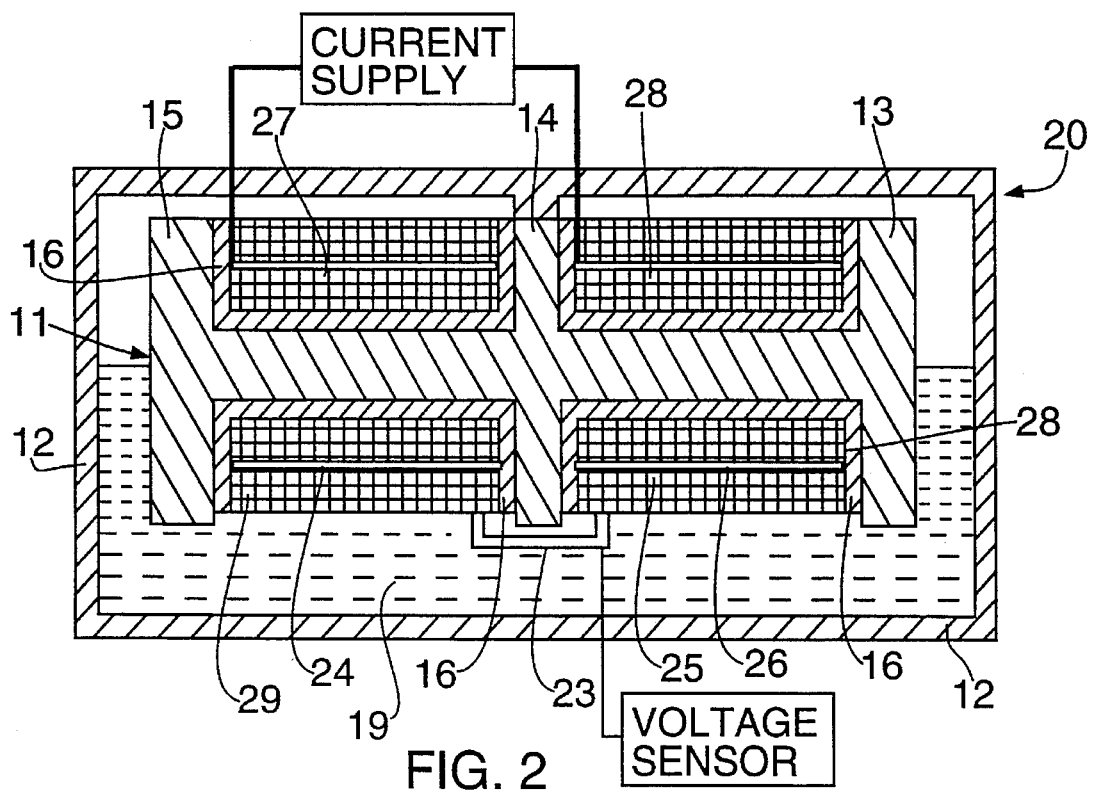

In the sensor 10 having first and second primary coils, 17 and 18, whether connected in series opposition or series aiding, the voltage must be correlated from a non-zero point of reference (as is apparent from a review of the graph in FIG. 3), which non-zero point of reference is defined when the sensor is in the horizontal position. To facilitate precise angular measurement, without the need to calibrate the system or correlate the readings output from same, a second embodiment of the invention utilizes pairs of primary and secondary coils, as illustrated in FIG. 2. With reference to FIG. 2, the tilt sensor, 20 has many of the same basic components as are found in the FIG. 1 embodiment. In order to facilitate understanding of this embodiment and of subsequently-described embodiments of the invention, like reference numerals are utilized for all components which are common to the embodiments, and recitation of the materials, connections, and functions of like components is not repeated, where such would be redundant and readily apparent to one having skill in the art upon a reading of the foregoing.

Referring to FIG. 2, the tilt sensor 20 of this embodiment comprises the ferromagnetic coil form 11 as was described with reference to FIG. 1, including flanges 13, 14 and 15 extending in the radial direction and defining two openings for the coils, with at least flange 14 being attached to housing 12. The openings may be lined with bobbins 16 of insulating material as discussed above. First primary coil 27 of insulated electrically conductive wire is wound about the opening defined by flanges 14 and 15 and is connected in series opposition at junction 22 to second primary coil 28 of insulated electrically conductive wire which is wound about the opening defined by flanges 14 and 13. An interlayer 24 of electrical insulation material, such as electrical tape is disposed about coil 27 and interlayer 26 of the same electrical insulation material is disposed about coil 28. First secondary coil 29 of insulated electrically conductive wire is wound over the interlayer 24, about first primary coil 27, in the opening defined by flanges 15 and 14 and is connected in series aiding at junction 23 to second secondary coil 25 of insulated electrically conductive wire wound over the interlayer 26, about second primary coil 28, in the opening defined by flanges 14 and 13. Sealed housing 12 is partially filled with ferromagnetic fluid 19 such that the coil form 11 is partially submerged in the ferromagnetic fluid.

In operation, a source of alternating current is connected to the terminals of coil 27 and coil 28 which are connected in series opposition causing current through first primary coil 27 to generate a magnetic flux and current through second primary coil 28 to generate a magnetic flux reversed in direction to the flux generated by first primary coil 27. In the horizontal position, therefore, the two magnetic fluxes will flow in the same direction through flange 14, into the ferromagnetic fluid 19, wherein the magnetic fluxes will separate into two equal flux flows, flowing in opposite directions around coil 27 and coil 28, into flanges 15 and 13 respectively, and back into coil form 11.

Since first secondary coil 29 is wound over first primary coil 27, and second secondary coil 25 is wound over second primary coil 28, the flux will pass through coil 29 and coil 25. Since first secondary coil 29 and second secondary coil 25 are connected in series aiding, and the fluxes flow in opposite direction, the voltage generated in coil 29 will cancel the voltage generated in coil 25, when the fluxes have the same magnitude. When the tilt sensor 20 is placed in the horizontal position, the flux flow around first primary coil 27 and first secondary coil 29 will be equal to the magnitude of the flux flow around second primary coil 28 and second secondary coil 25. Therefore, the output voltage measured by a meter connected across the circuit of secondary coils 29 and 25 will be zero. When tilt sensor 20 is tilted along its longitudinal axis, the flat bottom surface of housing 12 will not be in the horizontal position, but the ferromagnetic fluid 19 will stay horizontal due to gravity, and the amount of ferromagnetic fluid 19 between flange 14 and flange 15 will be different from the amount of ferromagnetic fluid between flange 14 and flange 13. Therefore, the voltage measured by a meter connected across the secondary circuit will increase and will be reversed in phase depending upon the direction of tilt.

Figure 4:
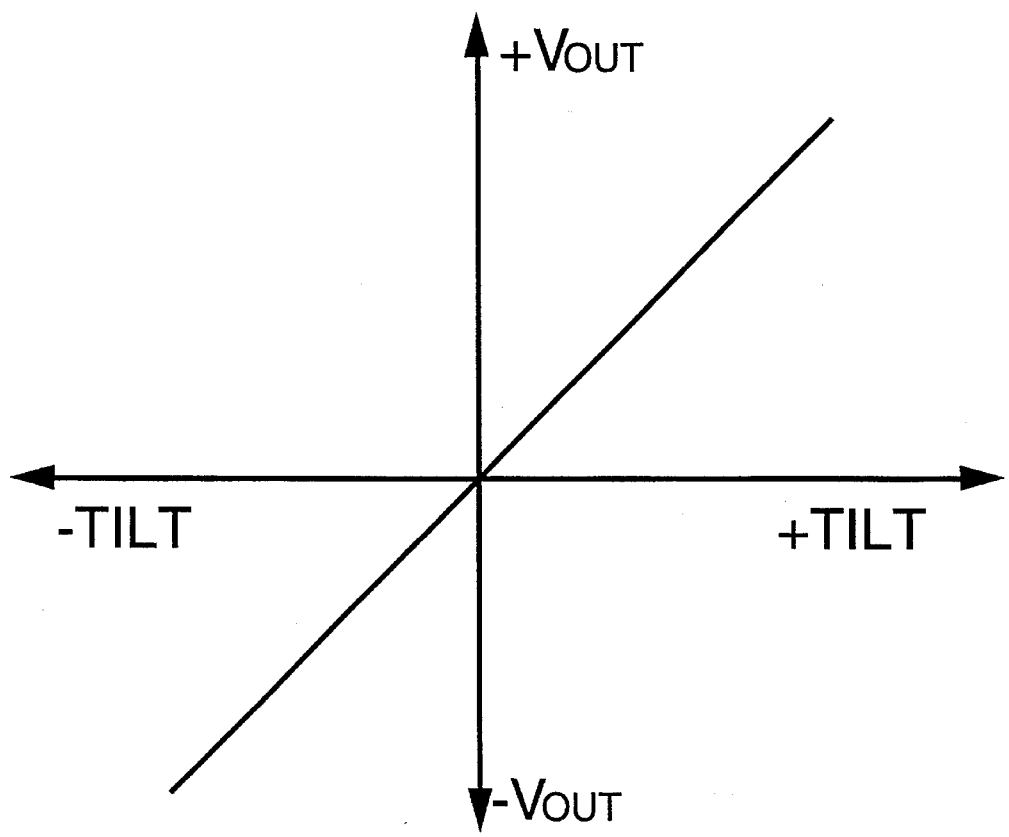
FIG. 4 is a graph illustrating the voltage output: tilt angle for the second embodiment of the invention.

FIG. 4 provides a graph of the output voltage of the secondary circuit as a function of tilt of the sensor. For this embodiment, a zero output is measured when the sensor is in the horizontal position; a positive voltage is registered when the sensor is tilted in one direction; and, a negative output is registered when the sensor is tilted in the opposite direction.

A housing 52 for another embodiment of the inventive tilt sensor is illustrated in FIG. 5. The housing 52 is fabricated of a plastic or non-ferromagnetic metal, such as a non-magnetic stainless steel, and has a circular outer wall 51 and a circular inner wall 53 which define outer and inner circles with an annular space therebetween (see FIG. 6). The housing comprises a cylindrical member having an annular channel between walls 51 and 53, which channel extends along the length 55 of the housing. Each end of the channel is sealed with seal plug 54, effectively a washer fabricated of ferromagnetic material, having a thickness equal to that of the outer wall [or coil form] to optimize the flux path, which is preferably fabricated of the same material as the housing. Ferromagnetic fluid 59 is disposed in the annular channel of housing 52 to partially fill the housing. FIG. 6 provides a cross-sectional view of the housing of FIG. 5 as taken along the plane A–A' of FIG. 5. As detailed with reference to the above-described embodiments, upon angular displacement of housing 52, the surface of the ferromagnetic fluid will remain horizontal under the influence of gravity. FIGS. 7 through 9 illustrate sensor embodiments having housing 52 and utilizing the shifting of a ferromagnetic fluid disposed therein to measure angular displacement of the housing.

FIG. 7 provides a tilt sensor 50 including cylindrical housing 52 having annular channel 58 which is partially filled with ferromagnetic fluid 59, as described with reference to FIG. 5. In the opening defined by the inner wall of the cylindrical housing having the annular channel, coextensive coil form 56 is located along the longitudinal axis of the housing. Coil form 56 has flange ends which fit into the circular ends of the housing cylinder, attaching the coil form to the inner wall of the housing at the ends. Bobbin 57 is disposed about the coil form 56 and has bobbin flanges 61, 62, 63 and 64 which define three compartments or channels along the coil form. Primary coil 67 is wound about the center channel of the sensor, the channel being defined by flanges 62 and 63. As above, the primary coil is preferably an insulated, electrically conductive wire which is connected to receive an alternating current from an AC source (not shown). The alternating current will generate alternating magnetic flux flow through the center axis of coil form 56, through a first flange located at a first end of the coil form, through seal plug 54 at the first end, into and along the ferromagnetic fluid 59, into the seal plug 54 at the opposite end of the sensor, into flange 54 at the opposite end of the coil form, and back along the center axis of the coil form. The tilt sensor 50 is additionally provided with first and second secondary coils, 66 and 65. The first secondary coil, 66, is insulated electrically conductive wire which is wound about the bobbin in the channel defined by bobbin flanges 61 and 62. Second secondary coil 65 of insulated electrically conductive wire is wound about the bobbin in the channel defined by bobbin flanges 63 and 64. The first and second secondary coils are connected to one another in series opposition. Therefore, when an AC current is applied to primary coil 67, the voltage across the secondary circuit of the differential transformer, as measured by a meter connected across the secondary circuit (not shown) will be the result of the flux flow in each of the secondary coils 66 and 65. When the tilt sensor is in a horizontal position, the measured voltage will be zero. When the sensor is tilted, the ferromagnetic fluid will stay level due to gravity and, therefore, as above, the amount of ferromagnetic fluid 59 about one secondary coil will increase and the amount of ferromagnetic fluid about the other secondary coil will decrease, causing a change in the magnetic coupling between primary coil 67 and the secondary circuit. The change in magnetic coupling will cause an output voltage measured across the secondary circuit which voltage is a function of the angular displacement of the sensor along its longitudinal axis.

FIG. 8 provides another embodiment of the invention utilizing the cylindrical housing 52. In the FIG. 8 embodiment, the housing, channel, seal plugs, and ferromagnetic fluid are unchanged from the FIG. 7 embodiment. The coil form and associated coils, however, are configured differently and parallel the FIG. 1 sensor in materials and function. The sensor 150 has coil form 151 having a central axis and flanges 152, 153 and 154 extending radially from the central axis. Flanges 152 and 153 define a first opening in the coil form, while flanges 153 and 154 define a second opening. Bobbins 155 may optionally be included along the openings to provide additional insulation and facilitate winding of the coils. First primary coil 156 is wound about the coil form in the opening defined by flanges 152 and 153 and is connected at junction 158 in series opposition to the second primary coil 157 which is wound about the coil form in the opening defined by flanges 153 and 154. In operation, the FIG. 8 embodiment parallels the FIG. 1 embodiment whereby a non-zero reference value is determined when the sensor is in a first, horizontal position. Upon angular displacement of the sensor 150 along its longitudinal axis, the AC current applied to the primary coil circuit will generate magnetic flux paths as described for sensor 10, such that the impedance of coil 156 will not be equal to the impedance in coil 157 and the voltage measured at junction 158 will be either higher or lower than the non-zero horizontal reference value in an amount which is indicative of the angle of tilt.

FIG. 9 illustrates another embodiment of the invention wherein the cylindrical housing 52 is utilized. In the FIG. 9 embodiment, the coil form 151 has the same configuration as in the FIG. 8 embodiment, wherein flanges 152 and 153 define a first opening and flanges 153 and 154 define a second opening. As with the other sensor embodiments, and particularly the FIG. 2 sensor which parallels the coil form and circuitry of the present embodiment, the openings in the coil form may optionally be provided with bobbins 155 for additional insulation and ease of winding application. A first primary coil 161 is wound about the coil form in the opening defined by flanges 152 and 153, and is connected in series opposition at junction 167 to second primary coil 162 which is wound about the coil form in the opening defined by flanges 153 and 154. Interlayer 165 is provided over first primary coil 161 and interlayer 166 is provided over second primary coil 162, each interlayer being fabricated of electrical tape or like insulating material. First secondary coil 163 is wound over the interlayer 165 in the opening defined by flanges 152 and 153 and is connected at junction 168 in series aiding to second secondary coil 164 which is wound over interlayer 166 in the opening defined by flanges 153 and 154. As noted in the description of the FIG. 1 and FIG. 2 embodiments, the dimensions of the coil form relative to the housing and the amount of ferromagnetic fluid are optimized to provide a low reluctance magnetic path. In the FIGS. 7–9 sensors, the thickness of channel 58 is also selected to provide optimal fluid depth for the paths.

In operation, the FIG. 9 sensor parallels the FIG. 2 embodiment. An AC current applied to the primary circuit generates the magnetic flux paths which pass through the secondary coils. A meter attached across the secondary circuit will detect a zero voltage when the sensor is in the horizontal position due to cancellation of the equal fluxes. Upon angular displacement of the sensor along its longitudinal axis, however, the meter will detect a positive voltage when the sensor is tilted in one direction and a negative voltage when the sensor is tilted in the opposite direction.

FIGS. 10A and 10B illustrate the inventive sensor mounted in clamps such as rubber dam clamps, adapted to engage a tooth for which angular displacement is to be measured. In FIG. 10A, the sensor 110 is held by a metal clip 111 which is soldered or cemented to clamp 112 which engages the tooth 114 for which angular displacement is to be measured. FIG. 10B provides an overhead view of the same arrangement.

FIG. 11 illustrates the inventive sensor 120 for mounting in a metal clip 123 which is attached to a member 122 adapted to engage the implant fixture 121 via screw 124 for measuring the angular displacement of the implant fixture.

The clip ideally has a central circular opening to allow a screw to slip through to attach member 122 to fixture 121 before the sensor is clipped in place.

Although the inventive sensor has been described with specific reference to several embodiments and mountings, it will be apparent to one having skill in the art, upon a reading of this patent, that modifications and materials adjustments may be effected without departing from the spirit and scope of the invention as defined by the appended claims.

What is claimed is:

1. A sensor for measuring the angular displacement of a body comprising:

a sealed housing;

at least one current path means disposed in said housing;

means for applying current to said current path means;

variable low reluctance magnetic flux path about said current path means, comprising a ferromagnetic frame mounted in said housing, about which frame said at least one current path means is disposed and ferromagnetic fluid disposed in said sealed housing, in which fluid said ferromagnetic frame is partially submerged, the level of said fluid relative to said current path means varying in response to angular displacement along the longitudinal axis of said sensor; and sensing means for measuring the output from said current path means as a function of variations in said variable magnetic flux path.

2. The sensor of claim 1 wherein said at least one current path means comprises a primary circuit comprising:

first primary winding of wire; and second primary winding of wire connected to said first primary winding in series aiding.

3. The sensor of claim 1 wherein said at least one current path means comprises a primary circuit comprising:

first primary winding of wire; and second primary winding of wire connected to said first primary winding in series opposition.

4. The sensor of claim 4 further comprising a secondary circuit comprising:

first secondary winding of wire disposed about and insulated from said first primary winding of wire; and second secondary winding of wire disposed about and insulated from said second primary winding of wire, said second secondary winding connected to said first secondary winding in series aiding.

5. The sensor of claim 4 wherein said means for applying current is connected to said primary circuit and wherein said sensing means is connected to said secondary circuit.

6. The sensor of claim 1 wherein said sealed housing comprises a cylindrical housing having an outer cylinder, an inner cylinder equal in length to said outer cylinder and having a diameter which is smaller than the diameter of said outer cylinder, and seal means connecting said inner cylinder to said outer cylinder to form a sealed annular channel between said inner and said outer cylinders.

7. The sensor of claim 6 wherein said variable magnetic flux path comprises:

ferromagnetic frame means mounted in the opening of said inner cylinder, about which frame said at least one current path means is disposed; and ferromagnetic fluid partially filling said sealed annular channel, wherein said path changes due to fluid flow upon angular displacement along the longitudinal axis of the sensor housing.

8. The sensor of claim 6 wherein said current path means comprises a primary circuit comprising:

first primary winding of wire; and second primary winding of wire connected to said first primary winding in series aiding.

9. The sensor of claim 6 wherein said current path means comprises a primary circuit comprising:

first primary winding of wire; and second primary winding of wire connected to said first primary winding in series opposition.

10. The sensor of claim 9 further comprising a secondary circuit comprising:

first secondary winding of wire disposed about and insulated from said first primary winding; and second secondary winding of wire disposed about and insulated from said second primary winding and connected to said first secondary winding in series aiding.

11. The sensor of claim 10 wherein said means for applying current is connected to said primary circuit and said sensing means is connected to said secondary circuit.

12. A method for sensing angular displacement of a body with a sensor comprising current path means and variable low reluctance magnetic flux path means, said flux path means comprising ferromagnetic fluid, the level of which in relation to said current path means varies in response to angular displacement along the longitudinal axis of the sensor; comprising:

applying an alternating current to said current path means;

sensing the output of said current path means as a function of variation in said variable low reluctance magnetic flux path means due to angular displacement along the longitudinal axis of the sensor and the consequent displacement of said ferromagnetic fluid.

13. A sensor for measuring angular displacement of a small body comprising:

a sealed housing;

a ferromagnetic frame having a central axis and being mounted in said sealed housing;

a first primary winding of wire disposed about a first portion of said ferromagnetic frame and insulated from said frame;

a second primary winding of wire disposed about a second portion of said ferromagnetic frame and insulated from said frame and said first portion of said frame, said second primary winding being connected to said first primary winding to form a primary circuit;

ferromagnetic fluid partially filling said housing to a level at which said ferromagnetic frame is partially submerged in said fluid defining low reluctance magnetic paths about said first and second primary windings in said frame and said fluid;

means for applying an alternating current to said first primary circuit; and means for measuring the voltage output from said sensor as a function of the applied alternating current and of the angular orientation of the ferromagnetic fluid in said housing relative to said first and said second primary coils.

14. The sensor of claim 13 wherein said first primary winding is connected to said second primary winding in series aiding.

15. The sensor of claim 14 wherein said first primary winding is connected to said second primary winding is series opposition.

16. The sensor of claim 15 additionally comprising a secondary circuit comprising:

first secondary winding disposed about and insulated from said first primary winding in said first portion of said frame; and second secondary winding disposed about and insulated from said second primary winding in said second portion of said frame, said second secondary winding connected in series aiding to said first secondary winding; and wherein said means for measuring the voltage output from said sensor is connected across said secondary circuit.

17. The sensor of claim 16 wherein said ferromagnetic frame comprises first, second and third flange members radiating from the central axis of said frame and wherein said first primary winding and said first secondary winding are disposed in a first channel of said ferromagnetic frame defined by first and second flange members and said second primary winding and said second secondary winding are disposed in a second channel of said ferromagnetic frame defined by said second and third flange members.

18. The sensor of claim 17 further comprising insulated bobbin means disposed in said first and said second channels of said frame.

19. The sensor of claim 16 wherein said sensor provides measurement of the angular displacement of a body in the mouth of a dental patient and wherein said sensor further comprises means for engaging said body, said means attached to said sensor.

20. The sensor of claim 13 wherein said ferromagnetic frame comprises first, second and third flange members radiating from the central axis of said frame and wherein said first primary winding is disposed in a first channel defined by first and second flange members and said second primary winding is disposed in a second channel defined by said second and third flange members.

21. The sensor of claim 20 further comprising insulated bobbin means disposed in said first and said second channels of said frame.

22. The sensor of claim 13 wherein said sensor provides measurement of the angular displacement of a body in the mouth of a dental patient and wherein said sensor further comprises means for engaging said body, said means attached to said sensor.

23. A sensor for measuring angular displacement of a small body comprising:

a cylindrical housing comprising inner and outer sleeve members of equal length, said inner sleeve member having a diameter which is smaller than the diameter of said outer sleeve member and being connected to said outer sleeve member at its ends so as to define a sealed annular channel between said inner and outer sleeve members;

ferromagnetic fluid disposed in said annular channel, said fluid partially filling said annular channel;

ferromagnetic frame means having a central axis and being mounted in the inner sleeve of said cylindrical housing;

first primary winding of wire disposed about a first portion of said ferromagnetic frame and insulated from said frame;

second primary winding of wire disposed about a second portion of said ferromagnetic frame and insulated from said frame and said first primary winding, said second primary winding being connected to said first primary winding to form a primary circuit;

means for applying an alternating current to said first primary circuit; and means or measuring the voltage output from said sensor as a function of the applied alternating current and of the angular orientation of the ferromagnetic fluid in said housing relative to said ferromagnetic frame and said coils.

24. The sensor of claim 23 wherein said first primary winding is connected to said second primary winding in series aiding.

25. The sensor of claim 23 wherein said first primary winding is connected to said second primary winding in series opposition.

26. The sensor of claim 25 additionally comprising a secondary circuit comprising:

first secondary winding of wire disposed about and insulated from said first primary winding in said first portion of said frame; and second secondary winding of wire disposed about and insulated from said second primary winding in said second portion of said frame, said second secondary winding connected in series aiding to said first secondary winding; and wherein said means for measuring the voltage output from said sensor is connected across said secondary circuit.

27. The sensor of claim 26 wherein said ferromagnetic frame comprises first, second and third flange members radiating from the central axis of said frame and wherein said first primary winding and said first secondary winding are disposed in a first channel of said ferromagnetic frame defined by said first and second flange members and said second primary winding and said second secondary winding are disposed in a second channel defined by said second and third flange members.

28. The sensor of claim 27 further comprising insulated bobbin means disposed in said first and said second channels of said frame.

29. The sensor of claim 26 wherein said sensor provides measurement of the angular displacement of a body in the mouth of a dental patient, said sensor further comprising means for engaging said body, said means being attached to said sensor.

30. The sensor of claim 23 wherein said ferromagnetic frame comprises first, second and third flange members radiating from the central axis of said frame and wherein said first primary winding is disposed in a first channel of said ferromagnetic frame defined by first and second flange members and said second primary winding is disposed in a second channel of said ferromagnetic frame defined by said second and third flange members.

31. The sensor of claim 30 further comprising insulated bobbin means disposed in said first and said second channels of said frame.

32. The sensor of claim 23 wherein said sensor provides measurement of the angular displacement of a body in the mouth of a dental patient, said sensor further comprising means for engaging said body, said means being attached to said sensor.

33. A sensor for measuring angular displacement of a small body comprising:

a sealed housing;

a ferromagnetic frame mounted in said sealed housing and having first, second and third portions thereof;

a first secondary winding of wire disposed about a first portion of said ferromagnetic frame and insulated from said frame;

a second secondary winding disposed about the third portion of said ferromagnetic frame and insulated from said frame and said second portion of said frame, said second secondary winding being connected to said first secondary winding in series opposition to form a secondary circuit;

a first primary winding of wire disposed about the second portion of said ferromagnetic frame between said first and third portions and insulated from said frame and said secondary circuit;

ferromagnetic fluid partially filling said housing to a level at which said ferromagnetic frame is partially submerged in said fluid;

means for applying an alternating current to said first primary winding; and means for measuring the output voltage from said secondary circuit as a function of the angular orientation of the ferromagnetic fluid in said housing relative to said ferromagnetic frame and said coils.

* * * * *